US012543946B2

(12) United States Patent
Hofeldt

(10) Patent No.: US 12,543,946 B2
(45) Date of Patent: Feb. 10, 2026

(54) MONOCULAR FOVEAL FOCAL WHITE AND COLOR LIGHT PHOTOBLEACHING

(71) Applicant: Albert John Hofeldt, Miami Beach, FL (US)

(72) Inventor: Albert John Hofeldt, Miami Beach, FL (US)

( * ) Notice: Subject to any disclaimer, the term of this patent is extended or adjusted under 35 U.S.C. 154(b) by 529 days.

(21) Appl. No.: 17/966,865

(22) Filed: Oct. 16, 2022

(65) Prior Publication Data

US 2023/0145621 A1 May 11, 2023

Related U.S. Application Data

(60) Provisional application No. 63/277,180, filed on Nov. 9, 2021.

(51) Int. Cl.
*A61B 3/02* (2006.01)
*A61B 3/06* (2006.01)
*A61B 3/08* (2006.01)

(52) U.S. Cl.
CPC .............. *A61B 3/022* (2013.01); *A61B 3/063* (2013.01); *A61B 3/08* (2013.01)

(58) Field of Classification Search
CPC ............ A61B 3/022; A61B 3/063; A61B 3/08
USPC .......................................................... 351/239
See application file for complete search history.

(56) References Cited

U.S. PATENT DOCUMENTS 11,026,573 B1 * 6/2021 Hofeldt .................. A61H 5/005

* cited by examiner

*Primary Examiner* — Brandi N Thomas
*Assistant Examiner* — Leonidas Boutsikaris

(57) ABSTRACT

Utilizing color light for focal stimulation of the macula for photobleaching and dark adaptation provides a means to isolate the recovery ability of different types of cones. Having the ability of selectively analyzing the recovery of different types of cones opens the opportunity to determine the effect of disease on cone type for diagnosis and monitoring of disease severity. An endpoint target with a noticeable difference between the center of the target and the peripheral ring of the target at endpoint is described.

8 Claims, 5 Drawing Sheets

Prior Art

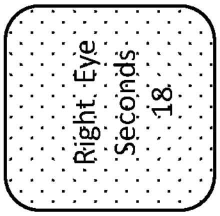
Figure 7d
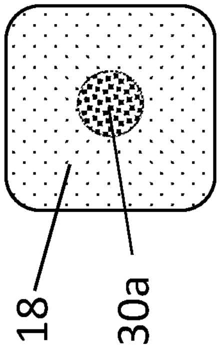
Figure 7a
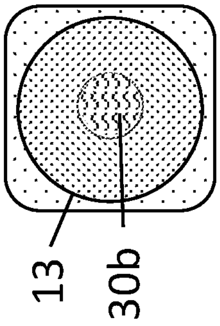
Figure 7b
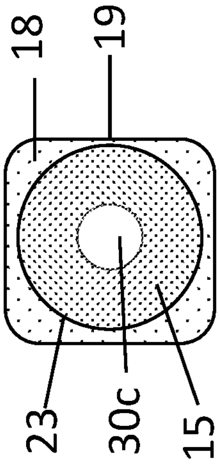
Figure 7c
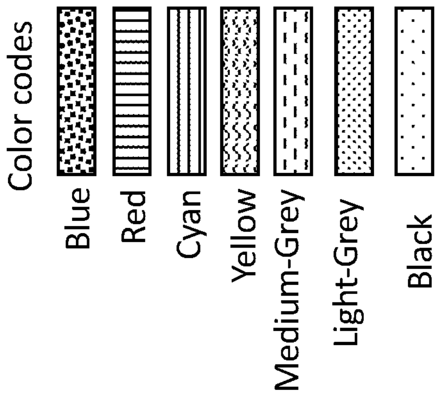

MONOCULAR FOVEAL FOCAL WHITE AND COLOR LIGHT PHOTOBLEACHING

CROSS REFERENCE TO RELATED APPLICATIONS

Provisional patent application 63/277,180 dated Nov. 9, 2021

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATED-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURE BY THE INVENTOR OR A JOINT INVENTOR

Not Applicable

BACKGROUND OF THE INVENTION

Field of the Invention

This invention relates to monocular vision testing. To be specific, this invention pertains to light adaptation of center of one eye with white or color light and measuring the time for the afterimage to disappear with regain of cone function, dark adaptation.

Related Art

U.S. Pat. No. 11,026,573. Patent Date Jun. 8, 2021. Monocular and Binocular Relative Focal Photo-Stress

BRIEF SUMMARY OF THE INVENTION

Light adaptation, also known as photopigment bleaching or photobleaching, reduces the sensitivity of photoreceptors to light. The reversal of light adaptation occurs during dark adaptation of cones where the photochemical reactions regenerate photopigments to restore vision. Originally, dark adaptation of the peripheral and central retina was measured by the visual threshold of seeing light. When dark adaptation is used to clinically test the central macula the test is called “photostress recovery” when regain of function is the return of visual acuity or contrast sensitivity. Generally, the bleaching light for photostress recovery has been diffuse stimulation of the retina, and apparently does not produce a recognizable afterimage. Dark adaptation of the peripheral retina which Concentrate on rods uses a focused bleaching light of small diameter which leaves a blinding afterimage, the speed of resolution of afterimage is the parameter used for dark adaptation measurement. Hofeldt patent U.S. Pat. No. 11,026,573 was the first to describe using the resolution of the afterimage following focal foveal bleaching to measure regain of cone function. Since focal fovea bleaching and peripheral retinal bleaching both rely on resolution of afterimage to measure regain of function, it is logical to group them together in the dark adaptation category, since neither have characteristics of photo-stress recovery, recovery of visual acuity or contrast sensitivity. In this application, photoreceptor regain of function following an afterimage will be termed dark adaptation.

In this application, bull’s eye refers to the center of a concentric figure where the center is demarcated by a circular line. As will be illustrated in the drawings, the endpoint need not be a bull’s eye target, it can have any background shape and the center can be an image without a circular demarcation line. The center may be a stand-alone image such as such an apple, a tomato, or any design. I have discovered a novel endpoint, not when the center appears equal to the peripheral ring at endpoint as in Hofeldt patent U.S. Pat. No. 11,026,573, but when the center appears just noticeably brighter than the peripheral ring at endpoint. This is possible by setting the brightness of the center or the point of focus of the endpoint target brighter than other elements of the target. Immediately after bleaching one eye, the endpoint target appears for viewing by the patient. The darkness of the afterimage masks the bright center until the dark adaptation photochemical reaction reactivates the cones to regains vision causing the afterimage to disappear and reveal that the bright center is brighter than the peripheral ring. The center and the peripheral ring can be shades of grey if the brightness difference between the center and peripheral ring is great enough to notice a brightness different. Even though the center may not be of white, it appears white at the endpoint of no-noticeable difference to notable difference endpoint because the human eye interprets the brightest element in the field of vision as white. Weber’s law teaches that two stimuli differing by approximately 10% is the point where people are stirred to respond to the stimulus. For room lighting, 7.4% brightness difference is detectable, and others found the detectability of illuminance decreases and illuminance increases were 8% and 6% respectively. (https://doi.org/10.1364/OE.24.00A885). For the endpoint in Hofeldt patent U.S. Pat. No. 11,026,573 the perceptual change is from a noticeable difference (dark afterimage masking the bull’s eye center) to no-noticeable difference (bull’s eye center is unmasked when the afterimage fades to reveal that the center and the peripheral ring appear of equal brightness) which I found to be a less obvious endpoint than changing from no difference to a perceivable difference. My experiments have shown, the endpoints for noticeable to no-noticeable difference varied 12% more than for no-noticeable to noticeable difference in 5 subjects tested.

The Hofeldt patent U.S. Pat. No. 11,026,573 does not specify the color of the bleaching light stimulus during light adaptation. The bleaching light is specified as “a focal light beam of a diameter subtending an angle on the macula of less than that of a 20/400 symbol”. I have discovered that bleaching the macula with light of different wave lengths (colors), the afterimage appears as the complementary color to the bleaching light. This produces a dramatic appearing afterimage where the color and brightness of the target center stands out in contrast to the brightness of the background. An example of the complementary color change during bleaching is that a red light bleaching to a cyan color afterimage as in FIG. 8*a-c*. The reason for this is that the red light selectively bleaches the red cones which allows the unbleached blue and green cones to express their combined color of cyan (FIG. 8*b*) until the red cones recover, at which time the observed color turns to white (FIG. 8*c*). A blue light stimulus yields a yellow afterimage (unbleached red and green cones). A green light stimulus yields a purple afterimage (unbleached red and blue cones). Conversely for the complimentary colors, a cyan color stimulus yields a red afterimage (bleached blue and green cones), a yellow stimulus yields a blue afterimage (bleached red and green cones), and a purple stimulus yields a green afterimage (bleached red and blue cones). In general, the color of the afterimage is complementary to the stimulus color. Any color of light can be used. A benefit of bleaching with other than white light is the obviousness of change to white at endpoint and the ability to study the response of each cone type to dark adaptation in health and disease.

DETAILED DESCRIPTION OF THE INVENTION

Prior art of U.S. Pat. No. 11,026,573 is depicted in FIGS. 1-3 where a dark adaptation (photo-stress) application is presented on a graphic display device 2 having a black backdrop without the use of a stereo viewer. This embodiment requires the patient to cover or close the eye not being tested. As seen in FIG. 1, focal light stimulus 1 produces impression 3 of perception 4. In FIG. 2 recovery time is being measured as the center 5*a* of the bull's eye approaches the same brightness as the peripheral ring 6 of perception 7. In FIG. 3 recovery is complete as illustrated by equal brightness of center 5*c* and peripheral ring 9 in perception 10. FIGS. 4, 5 and 6 shows graphic display device 2 housed within stereo viewer 11 having viewing ports 12*a* and 12*b*. The light adaptation (stimulus) and dark adaptation (recovery) is the same as described for FIGS. 1-3.

FIG. 4 illustration white focal light stimulus 1 of digital display device 2 producing white impression 3 of perception 4. FIG. 5 depicts the afterimage masking the bull's eye white center 5*a* and causing white center 5*b* to appear darker than white peripheral ring in impression 6 of perception 7. The afterimage slowly disappears as the cones regenerate photopigment to restore vision, a process called dark adaptation. As seen in FIG. 6, once the vision returns, bull's eye white center 5*a* appears white as seen in impression 5*c* of perception 10, the same color as peripheral ring 9 in perception 10.

My first embodiment is illustrated in FIGS. 7*a*-9*c* and utilizes focal white or color light for selective bleaching of the photoreceptor in the fovea of one eye, the central area of the retina subtending an angle of less than a 20/400 Snellen chart letter. The focal bleaching light is a graphic object filled with white or color using RGB palette on a black backdrop. The endpoint frame 19 is critical for providing the most precise endpoint and is best illustrated in FIG. 7*c*. Endpoint frame 19 consists of black backdrop 18, endpoint target 23 with light-grey peripheral ring 15 and white center 30*c*. In FIG. 7*a* is illustrated blue circle 30*a* focal bleaching light which is viewed by the subject for a specified bleaching time, typically 30 seconds (programs range from 15 to 300 seconds), when after the presentation app transitions automatically to endpoint target 13 of FIG. 7*b* for recovery phase timing. In FIG. 7*b* is yellow afterimage 30*b* masking white center 30*c* of the endpoint target 23. In FIG. 7*c*, afterimage 30*b* has resolved to reveal white center 30*c* (the endpoint), which stands out brightly in contrast to the darker light-grey peripheral ring 15 of endpoint target 23. Of note, center 30*c* is brighter than peripheral ring 15 of the endpoint target 23. The endpoint timer consists of a embed movie composed of numbers from 0 to 100 at 1 second intervals, set to start upon automatic transition after bleaching and programmed to stop the moment the subject taps the screen at endpoint, the tap also reveals the timer readout by the disappearance of a layer (endpoint target 23) secluding the timer as illustrated uncovered in FIG. 7*d*. In FIG. 8*a*-*b* red apple 40*a* bleaching light yields cyan 41*a* afterimage, in FIG. 9*a*-*b* white tomato 50*a* bleaching light yields grey 51*a* afterimage. Following afterimage resolution, endpoints FIGS. 8*c* and 9*c* shows bright white apple 42*a* and bright white tomato 52*a* in contrast to light-grey peripheral ring. These drawings illustrate that the bleaching light need not be a circle, it can be of any shape having the same area (subtends a Snellen 20/400 letter) and that the endpoint target need not to be a bull's eye and can be the same shape as the bleaching light.

Drifting of the afterimage is not addressed in Hofeldt patent U.S. Pat. No. 11,026,573. There is no companion image to serve as an anchor for the afterimage in the recovery phase while observing the endpoint target. Subjects have a natural tendency to gaze around the endpoint target while waiting for the afterimage mask to clear which causes the afterimage to follow their gaze. I have found an embedded movie playing within the endpoint center having symbols appear every 1-2 seconds (star 53 in FIGS. 9*b*-*c*, and FIGS. 11-12) attracts the attention of the subject and gives the subject a focusing anchor for the afterimage during dark adaptation. Keeping their eye on the changing symbols puts the afterimage centered over the endpoint target in preparation for triggering the endpoint. The movie is created in a movie app consisting of a sequence of symbols and numbers with running time from 45 to 60 seconds. The movie is then embedded into a presentation program, programmed to start automatically after bleaching, and to stop when the endpoint is triggered.

My preferred embodiment is illustrated in FIGS. 10-12 which is a graphic display device housed in a stereo viewer having a right and a left chamber. Stereo viewer 17 housing a graphic display device providing screen images, black backdrop 18 and sounds is depicted in FIG. 10 where red apple 40*a* is the bleaching light source and is seen as impression red apple 40*b* in perception 43. The program of the graphic display device may be programmed to repeatedly test the same eye or alternate the eyes being tested. In FIG. 11 afterimage 41*a* appears in endpoint target 13 as cyan apple 41*a* within light-grey peripheral ring 15 while masking white endpoint center 42*b* and appears in perception 44 as afterimage 41*b*. In FIG. 12 is endpoint target 13 showing unmasked white apple 42*b* standing out in contrast to light-grey peripheral ring 15 in perception 45, an obvious endpoint.

BRIEF DESCRIPTION OF DRAWINGS

FIG. 7*a*. Blue circular focal light on black backdrop of the graphic display device.

FIG. 7*b*. Yellow afterimage of the recovery phase following blue light stimulus.

FIG. 7*c*. White center of bullseye, yellow afterimage has resolved.

FIG. 7*d*. Timer in seconds appearing on the backdrop.

Figure 1:
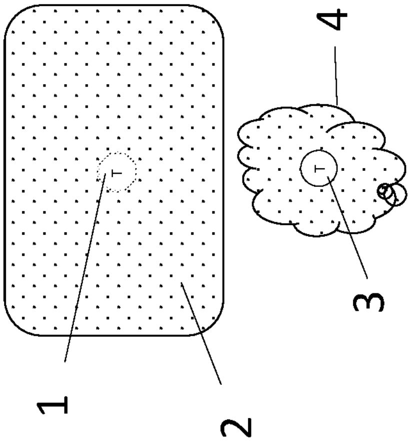
FIG. 1. Prior Art, Hofeldt patent U.S. Pat. No. 11,026,573 showing monocular focal light stimulation on a graphic display device and the observed perception.
Figure 2:
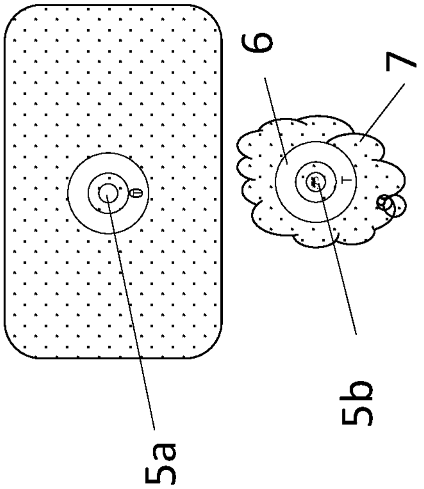
FIG. 2. Prior Art, Hofeldt patent U.S. Pat. No. 11,026,573 showing during recovery while viewing the bullseye endpoint target on a graphic display device and the observed perception.
Figure 3:
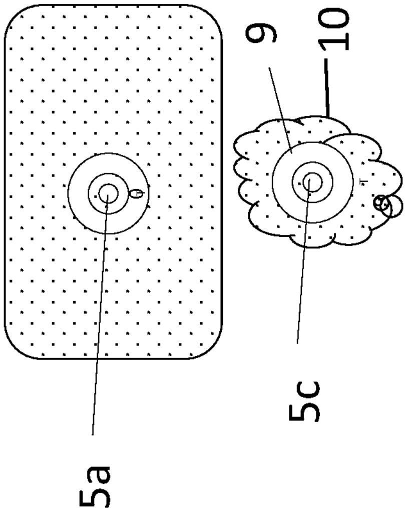
FIG. 3. Prior Art, Hofeldt patent U.S. Pat. No. 11,026,573 showing complete recovery while viewing the bullseye endpoint target on a graphic display device and the observed perception.
Figure 5:
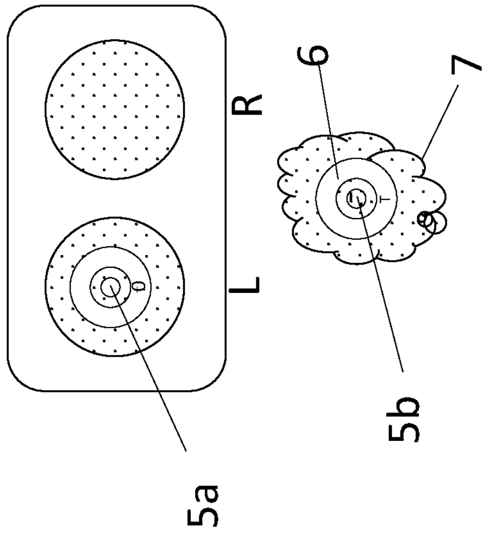
FIG. 5. Prior Art, Hofeldt patent U.S. Pat. No. 11,026,573 showing during recovery while viewing the bullseye endpoint target on a graphic display device within a stereo viewer and the observed perception.
Figure 6:
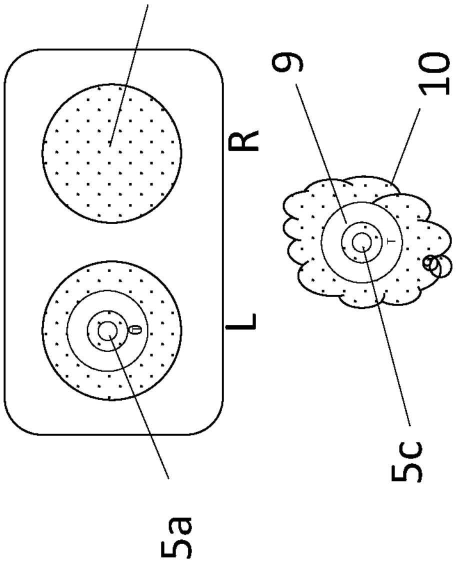
FIG. 6 Prior Art
FIG. 6. Prior Art, Hofeldt patent U.S. Pat. No. 11,026,573 showing complete recovery while viewing the bullseye endpoint target on a graphic display device within a stereo viewer and the observed perception.
Figure 4:
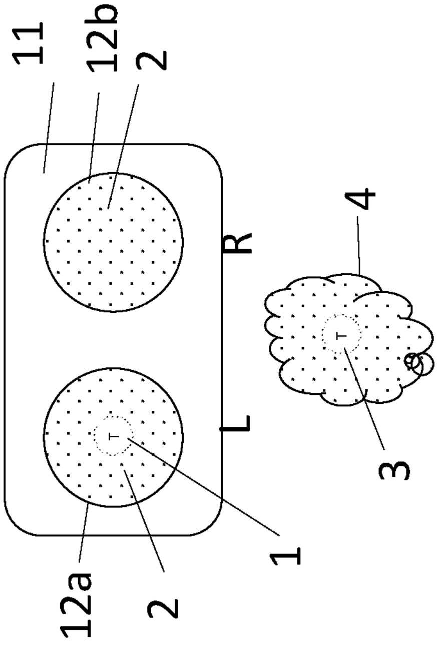
FIG. 4. Prior Art, Hofeldt patent U.S. Pat. No. 11,026,573 showing monocular focal light stimulation on a graphic display device within a stereo viewer and the observed perception.
Figure 9A:
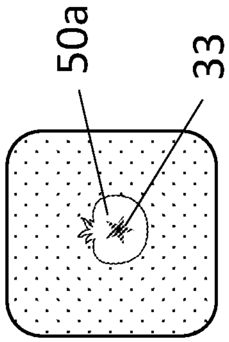
FIG. 9*a*. White circular focal light on black backdrop of the graphic display device.
Figure 9B:
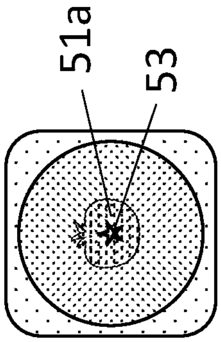
FIG. 9*b*. Grey afterimage of the recovery phase following white light stimulus.
Figure 9C:
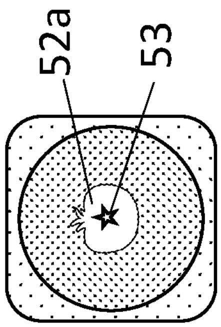
FIG. 9*c*. White center of bullseye, grey afterimage has resolved.
Figure 8A:
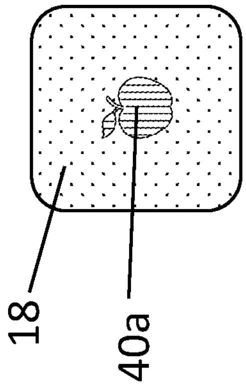
FIG. 8*a*. Red circular focal light on black backdrop of the graphic display device.
Figure 8B:
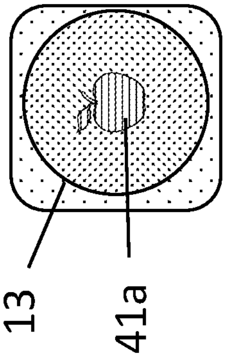
FIG. 8*b*. Cyan afterimage of the recovery phase following blue light stimulus.
Figure 8C:
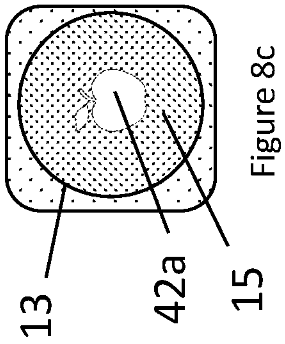
FIG. 8*c*. White center of bullseye, cyan afterimage has resolved.
Figure 11:
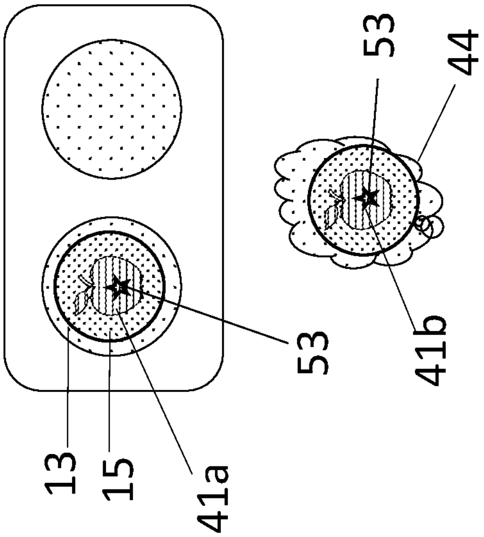
FIG. 11. Cyan afterimage of the recovery phase following blue light stimulus within the stereo viewer.
Figure 10:
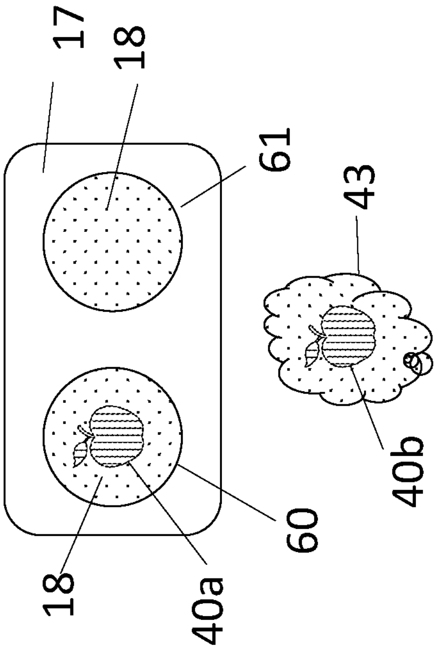
FIG. 10. Red circular focal light on black backdrop of the graphic display device within a stereo viewer.
Figure 12:
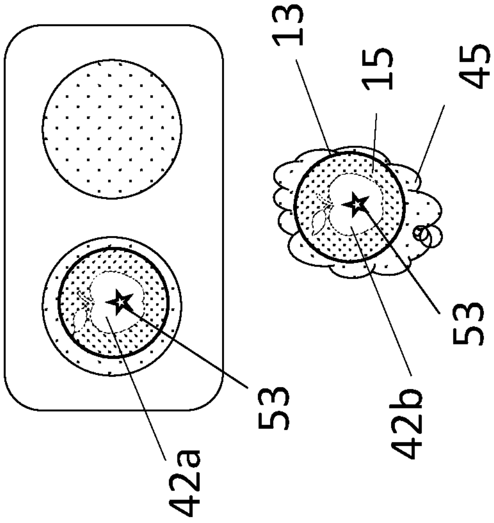
FIG. 12. White center of bullseye, cyan afterimage has resolved within the stereo viewer.

The invention claimed is:

1. A device for focal foveal monocular relative photobleaching comprising:

a. at least one frame in a graphic display device, the at least one frame having a black backdrop, an endpoint target with a peripheral ring and a center, the endpoint target being disposed within the black backdrop;

b. at least one photobleaching focal light source, the at least one photobleaching focal light source emitting a focal beam wherein the center of an endpoint target has a diameter subtending an angle of less than that of a symbol with a visual acuity setting at 20/400 configured to light adapt the fovea of at least one eye; and c. a digital display configured to show elapsed time of photobleaching recovery, wherein at an endpoint of the photobleaching recovery, after comparing the color of the center and the color of the peripheral ring the whiteness of the center appears whiter than the peripheral ring.

2. The device of claim 1, where the photobleaching focal light source is emitting white light.

3. The device of claim 1, where the photobleaching focal light source is emitting color light.

4. The device of claim 1, further comprising fixation symbols sequentially appearing within the center and running concurrently with an afterimage.

5. A device for focal foveal monocular relative photobleaching comprising:

a. a stereo viewer having a first frame and a second frame in a graphic display device, the stereo viewer having a left chamber and a right chamber opposite the left chamber, the first frame being disposed within the left chamber and the second frame being disposed within the right chamber;

b. each of the first frame and the second frame has a black backdrop, an endpoint target with a peripheral ring and a center, the endpoint target being disposed within the black backdrop;

c. a first photobleaching focal light source emitting a focal beam wherein the center of an endpoint target has a diameter subtending an angle of less than that of a symbol with a visual acuity setting at 20/400 configured to light adapt the fovea of at least one eye, and a second photobleaching focal light source emitting a focal beam wherein the center of an endpoint target has a diameter subtending an angle of less than that of a symbol with a visual acuity setting at 20/400 configured to light adapt the fovea of at least one eye, the first photobleaching focal light source being disposed within the left chamber and the second photobleaching focal light source disposed within the right chamber;

d. a digital display configured to show elapsed time of photobleaching recovery, wherein at an endpoint of the photobleaching recovery, following bleaching of the fovea, the view of the display reveals that the whiteness of the center becomes whiter than the peripheral ring.

6. The device of claim 5, where the first photobleaching focal light source and the second photobleaching focal light source is emitting white light.

7. The device of claim 5, where the first photobleaching focal light source and the second photobleaching focal light source is emitting color light.

8. The device of claim 5, further comprising fixation symbols sequentially appearing within the center and running concurrently with an afterimage.

* * * * *